(12) United States Patent
Miura et al.

(10) Patent No.: US 7,956,087 B2
(45) Date of Patent: Jun. 7, 2011

(54) COSMETIC COMPOSITION FOR SKIN AND WRINKLE IMPROVER

(75) Inventors: Kyoko Miura, Kanagawa (JP); Akinori Haratake, New York, NY (US)

(73) Assignee: Kao Corporation, Tokyo (JP)

( * ) Notice: Subject to any disclaimer, the term of this patent is extended or adjusted under 35 U.S.C. 154(b) by 673 days.

(21) Appl. No.: 11/918,657

(22) PCT Filed: Apr. 12, 2006

(86) PCT No.: PCT/JP2006/308394
§ 371 (c)(1),
(2), (4) Date: Oct. 17, 2007

(87) PCT Pub. No.: WO2006/115190
PCT Pub. Date: Nov. 2, 2006

(65) Prior Publication Data
US 2009/0069416 A1    Mar. 12, 2009

(30) Foreign Application Priority Data
Apr. 21, 2005    (JP) ................. 2005-124309

(51) Int. Cl.
*A01N 31/335* (2006.01)
(52) U.S. Cl. .......... 514/467; 549/430; 549/448
(58) Field of Classification Search ........ 549/448, 549/430; 514/467
See application file for complete search history.

(56) References Cited

U.S. PATENT DOCUMENTS

| | | | |
|---|---|---|---|
| 4,576,967 A | 3/1986 | Urata et al. | |
| 5,565,439 A | 10/1996 | Piazza et al. | |
| 5,659,052 A | 8/1997 | Ohashi et al. | |
| 5,753,707 A | 5/1998 | Hoshino et al. | |
| 5,801,258 A | 9/1998 | Ohashi et al. | |

FOREIGN PATENT DOCUMENTS

| | | |
|---|---|---|
| JP | 59-027844 A | 2/1984 |
| JP | 60-028944 A | 2/1985 |
| JP | 06-157507 A | 6/1994 |
| JP | 09-278732 A | 10/1997 |

OTHER PUBLICATIONS

S. Hamada et al., "Vitamin A and Derivatives thereof as Anti-wrinkle Material," Fragrance Journal, vol. 26, No. 4, Apr. 15, 1998, pp. 75-77.

*Primary Examiner* — Janet L. Andres
*Assistant Examiner* — Raymond Convington
(74) *Attorney, Agent, or Firm* — Foley & Lardner LLP

(57) ABSTRACT

The present invention is to provide skin cosmetics and anti-wrinkle agents which are excellent in reducing effect on wrinkle caused by photoaging.

Skin cosmetics and anti-wrinkle agents which comprise a sugar alcohol derivative represented by the following formula (1):

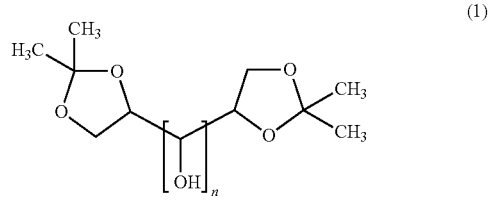

(1)

(wherein n is 1 to 5, preferably n=2.).

12 Claims, No Drawings

COSMETIC COMPOSITION FOR SKIN AND WRINKLE IMPROVER

TECHNICAL FIELD

The present invention relates to skin cosmetics and anti-wrinkle agents which have excellent effects of reducing wrinkles occurred due to aging, in particular, at an exposed portion, and have high safety.

BACKGROUND ART

Organs of all the creatures including human grow from birth, and gradually decline with age, then, functions thereof are deactivated. When the deactivated part exceeds a certain extent, the creature dies. The process that the functions thereof are gradually declining is called aging. Skin is directly affected by surroundings and has important functions to maintain circumstance of the inner part of living bodies. Although there is not so much that all of the skin is deactivated, skin is an organ that aging symptoms such as wrinkle, liver spot, dull, slack, etc. are liable to appear thereon, and these symptoms are particularly remarkable at an exposed portion that is exposed to sun light.

When aging of the skin proceeds, protection against stimulus such as oxidative stress, etc. becomes weak, which causes disturbance of internal circumstance of the skin, whereby the skin aging further proceeds. In particular, at the exposed portion, the skin is usually exposed to potent oxidative stress such as UV rays, etc., so that progress of the skin aging is remarkable. Such a change of the skin is referred to as "photoaging". Such a skin leads to undesirable conditions in cosmetic viewpoint that, for example, wrinkles become deep and large at the surface of the skin.

As a substance which has a reducing effect against wrinkles caused by the progress of photoaging, retinoic acid has been used for a prescription drug in the United States. However retinoic acid has potent side effects and involves problems in safety, so that it has not been admitted in Japan (see Non-Patent Literature 1). Accordingly, it has been desired to provide a wrinkle-reducing substance having high safety and sufficient effects.

On the other hand, a sugar alcohol (polyvalent alcohol) or ester and ether derivatives thereof which are widely existing in the natural world play an important role in life and activity of creatures. Also in a daily life, they have been widely used as a safe substance in the fields of detergent, foods, industrial chemicals, medical products, cosmetics, etc.

Also, ester and ether derivatives of the sugar alcohols such as diisopropylidene-D-mannitol have been used as a preparation intermediate (Patent Literature 1) of a surfactant utilized in the field of cosmetics, etc. However, no investigation has been conducted about a reducing effect of these substances on wrinkles.

Patent Literature 1: Japanese Patent No. 1521433
Non-Patent Literature 1: Sachio Hamada, Gen Fukuse, "Vitamin A and derivatives thereof as anti-wrinkle material", "FRAGRANCE JOURNAL", published by Fragrance Journal Ltd. on Apr. 15, 1998, vol. 26, No. 4, pp. 75-77

DISCLOSURE OF THE INVENTION

Problems to be Solved by the Invention

Thus, an object of the present invention is to provide an anti-wrinkle agent which is excellent in reducing effect on wrinkles which become tangible due to aging, in particular, markedly tangible at the exposed portion, and excellent in effects of maintaining healthy skin from a cosmetic view point.

Means to Solve the Problems

The present inventors have earnestly studied in view of the above-mentioned circumstances, and as a result, they have confirmed that the following anti-wrinkle agent has excellent effects of reducing wrinkles which had been tangible due to aging, in particular, markedly tangible at the exposed portion, and maintaining the skin healthy from a cosmetic viewpoint, and excellent in safety, whereby the present invention has been accomplished.

That is, the present invention is directed to a skin cosmetic which comprises a sugar alcohol derivative represented by the following formula (1).

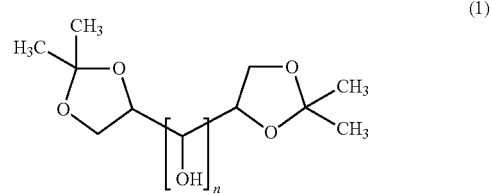

(wherein n is 1 to 5.)

Also, the present invention is directed to an anti-wrinkle agent which comprises a sugar alcohol derivative represented by the above-mentioned formula (1).

Effects of the Invention

The present invention can provide an anti-wrinkle agent and skin cosmetics, which are excellent in reducing effects on wrinkles occurred due to aging, in particular, at an exposed portion, and can maintain skins in a healthy state in view of skin science and cosmetic points.

BEST MODE TO CARRY OUT THE INVENTION

In the following, embodiments of the present invention are explained in detail.

For the sugar alcohol derivative represented by the following formula (1) to be used in the present invention, there may be used, for example, those produced by a method in which a sugar alcohol is reacted with acetone or dimethoxy propane in the presence of an acid catalyst, etc., or those commercially available from Tokyo Chemical Industry Co., Ltd., etc.

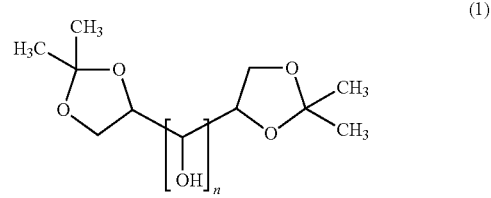

In the formula (1), n is preferably 1 to 5, more preferably n=2.

More specifically, there may be mentioned diisopropylidene-D-mannitol (1,2:5,6-Di-O-isopropylidene-D-mannitol), diisopropylidene-D-sorbitol (1,2:5,6-Di-O-isopropylidene-D-glucitol), etc. represented by the following formula (2), or diisopropylidene-xylitol (1,2:4,5-Di-O-isopropylidene-D-xylitol), etc. represented by the following formula (3).

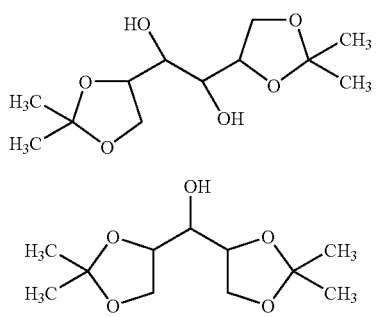

(2)

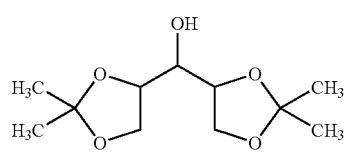

(3)

A formulation amount of the sugar alcohol derivative in the present invention is preferably 0.001 to 10.0 by mass (hereinafter, simply referred to as "%") based on the total amount of the skin cosmetics or the anti-wrinkle agent. It is more preferably 0.01 to 5.0%. If the formulation amount is less than the lower limit, the aimed effects of the present invention are not sufficient, while if it exceeds the upper limit, improvement in effects commensurate with the increased amount cannot be obtained so that it is not preferred.

Incidentally, into the skin cosmetics and anti-wrinkle agents of the present invention, a dye, perfume, antiseptic, surfactant, pigment, anti-oxidant, etc., may be optionally formulated within the range which can accomplish the objects of the present invention, in addition to the above components.

EXAMPLES

In the following, the present invention is explained in detail by referring to Examples and Comparative examples.

Wrinkle-reducing effects when a sample comprising a base material alone, or a sample comprising Compound 1; diisopropylidene-D-mannitol [this is represented by the above-mentioned formula (2), available from Tokyo Chemical Industry Co., Ltd., trade name: 1,2:5,6-Di-O-isopropylidene-D-mannitol] had been applied to photoaged skin, were examined according to the following test methods.

1. Experimental Animal 10-weeks old hairless mice at the start of the experiment were used with 10 mice per a group.

2. Measurement of Wrinkle-Reducing Effect 2-1. Photoaging Conditions and Measurement Method Photoaging was induced by irradiating skin with UVA and UVB once a day, five times a week for 8 weeks. An irradiation dose was increased every week from 20 J/cm$^2$, 25 J/cm$^2$ and 30 J/cm$^2$ for UVA, and from 20 mJ/cm$^2$, 30 mJ/cm$^2$ and 40 mJ/cm$^2$ for UVB, and after the 3$^{rd}$ week, the maximum dose was irradiated.

Wrinkle-reducing effects were evaluated by wrinkle score. The wrinkle score was graded according to the method of Bissett, et. al. (Photochem Photobiol 46: 367-378, 1987). That is, a size and a depth of the wrinkles were totally evaluated with naked eyes, with the maximum point as point 3. "Large and deep wrinkles can be confirmed" is rated as 3, "wrinkles can be confirmed" as 2, "no wrinkles can be confirmed" as 1, and "normal skin texture can be observed" as 0.

2-2. Samples and Experimental Method

A sample containing 1% of Compound 1 in 50% by volume aqueous ethanol solution (a base material) was prepared (Example 1). Also, a sample containing a base material alone was made as Comparative example 1.

First, 0.1 mL of each of these samples was applied on the dorsal skin (about 2.5 cm in diameter) of hairless mouse with a frequency of once a day, five times a week, from the 5$^{th}$ week after initiation of UV irradiation to 4$^{th}$ week after completion of the irradiation. And after completion of the applying, wrinkle score was graded. The wrinkle score was compared with the base material-applied group as a control.

(Results of Wrinkle score evaluation)

| | Group | Wrinkle score value |
|---|---|---|
| Example 1 | Compound 1 containing sample-applied group | 2.40 ± 0.10 |
| Comparative example 1 | Base material sample-applied group | 2.80 ± 0.20 |

(The values are an average value ± standard error)

Example 1 showed significantly low wrinkle score value as compared with that of Comparative example 1. This indicated that Compound 1 is effective to wrinkles induced by photoaging.

From the results of the present test, it can be understood that the anti-wrinkle agent (Example 1) containing diisopropylidene-D-mannitol (Compound 1) clearly has an effect of reducing wrinkles due to photoaging as compared with that of Comparative example 1.

Example 2

In this Example and Comparative example, skin creams having the following composition were prepared according to Preparation method as mentioned below, and used as a sample. Wrinkle-reducing effects were evaluated according to the following operation.

To 5 normal persons (female, 40 to 58-old) who, in questionnaires before the test, mentioned wrinkles at the outer corners of the eyes as a skin problem was applied a skin cream of Example 2 or Comparative example 2. Research on the condition of the skin (wrinkle) at the outer corners of the eyes was carried out by questionnaires according to the manner as mentioned below. Either one of the right or left outer corners of the eyes was decided as a portion to which the sample should be applied, and the other as a comparative portion to which no sample is applied. Each sample was applied on the wrinkle portion of the either one of the right or left outer corners of the eyes (about 4 cm$^2$, 2×2 cm with the outer corner of the eye as a center for each sample), with each about 0.2 mL twice a day, after washing the face in the morning and after bathing in the evening for continuously 2 months (60 days). Next, after completion of the final applying, the members answered questionnaires about the conditions of the skin (wrinkle) at the right and left outer corners of the eyes.

Composition of skin cream

| Components of starting material | Formulation amount (%) |
|---|---|
| Component A | |
| Bees wax | 2.0 |
| Stearic acid | 5.0 |
| Stearyl alcohol | 5.0 |
| Reduced lanorin | 2.0 |
| Squalene | 20.0 |
| Sorbitan monostearate | 3.0 |
| Polyoxyethylene (20) sorbitan monostearate | 3.0 |
| Propylene glycol | 5.0 |

-continued

| Composition of skin cream | |
|---|---|
| Components of starting material | Formulation amount (%) |
| Component B | |
| Methyl paraben | 0.2 |
| Purified water | Remainder |
| Component C | |
| Compound 1 | 1.0 (Example 2) or 0 (Comparative example 2) |
| Total | 100 |

Preparation Method

Compound 1 which is Component C was added to Component B, and each of Components A and B was dissolved by heating to 80° C., and then mixed. The mixture was cooled to 30° C. under stirring to prepare respective skin creams.

Based on the results of questionnaires, in respective items regarding the condition of skin (wrinkle), the number of persons who answered that the skin cream of Example 2 is more effective than that of Comparative example 2 is shown below.

| Item | Number of person (number) |
|---|---|
| Wrinkle became not conspicuous | 4 |
| Skin became soft | 4 |
| Skin became elastic | 4 |
| Skin became glowing | 4 |
| Skin became light | 3 |

From the results of this test, it can be understood that the skin cream of Example 2 clearly reduces wrinkle as compared with that of Comparative example 2, and that softness or elasticity of skin, which is worsen by photoaging, is also improved. Also, no skin abnormality such as stimulus or itching, etc. due to the skin cream of the present invention was observed.

Example 3

A skin lotion having the following composition was prepared according to a conventional manner, and was used for 2 weeks or longer by 20 normal persons (female, 42 to 58-old) who, in questionnaires before the test, mentioned wrinkles at the outer corners of the eyes as a skin problem. Research was carried out by questionnaires.

| Composition of skin lotion | |
|---|---|
| Components of starting material | Formulation amount (%) |
| Ethanol | 8.0 |
| Polyoxyethylene (60) hydrogenated castor oil | 0.3 |
| Polyoxyethylene (20) sorbitan monolaurate | 0.1 |
| Glycerin | 1.0 |
| Polyethylene glycol 4000 | 0.1 |
| Disodium phosphate | 0.09 |
| Monopotassium phosphate | 0.03 |
| Disodium edetate | 0.02 |

-continued

| Composition of skin lotion | |
|---|---|
| Components of starting material | Formulation amount (%) |
| Methyl paraben | 0.1 |
| Compound 1 | 1.0 |
| Purified water | remainder |
| Total | 100 |

Skin lotion of Example 3 was used by the members and research was carried out by questionnaires. The results are shown below. Incidentally, the results are based on the questionnaires consisted of following items with respect to the conditions of wrinkle, and show the number of persons who answered "yes" with respect to each item comparing the conditions before use and after use.

| Item | Number of person (number) |
|---|---|
| Wrinkle became not conspicuous | 17 |
| Size of wrinkle became small | 15 |
| Number of wrinkles reduced | 6 |
| Number of wrinkles increased | 0 |

From the results of this test, it can be understood that the skin lotion of Example 3 reduces wrinkles due to photoaging. Almost all the members feel that wrinkles became not conspicuous as compared with the condition before use, and as a factor thereof, there are mentioned reduction of a size of wrinkles rather than reduction of the number of wrinkles. Also, no skin abnormality such as stimulus, itching, etc. due to the skin lotion of the present invention was observed.

Example 4

Milky Lotion

A milky lotion of the present invention was prepared with the following composition according to a conventional manner.

| Components of starting material | Formulation amount (%) |
|---|---|
| Hydrogenated lecithin | 1.0 |
| Cholesterol | 0.5 |
| Squalane | 1.0 |
| Octyldodecyl myristate | 3.0 |
| Methylcyclopolysiloxane | 11.0 |
| Dipropylene glycol | 4.0 |
| 1,3-Butylene glycol | 4.0 |
| Glycerin | 7.0 |
| Diglycerin | 2.0 |
| Polyethylene glycol 4000 | 5.0 |
| Methyl paraben | 0.1 |
| Disodium edetate | 0.02 |
| Potassium hydroxide | Suitable amount |
| Xanthan gum | 0.01 |
| Alkyl acrylate/methacrylate copolymer | 0.08 |
| Carboxyvinyl polymer | 0.3 |
| Compound 1 | 1.0 |
| Perfume | 0.01 |
| Purified water | remainder |
| Total | 100 |

This milky lotion showed good results in the above-mentioned test.

Example 5

Day Essence

A day essence of the present invention was prepared with the following composition according to a conventional manner.

| Components of starting material | Formulation amount (%) |
| --- | --- |
| Ethanol | 10.0 |
| Methyl paraben | 0.1 |
| Polyoxyethylene (20) sorbitan monolaurate | 0.4 |
| Polyoxyethylene (60) hydrogenated castor oil | 0.8 |
| Methylcyclopolysiloxane | 2.0 |
| Methylphenylpolysiloxane | 0.5 |
| Squalane | 0.5 |
| Disodium edetate | 0.02 |
| Polyethylene glycol 4000 | 6.0 |
| Glycerin | 10.0 |
| Dipropylene glycol | 4.0 |
| Xanthan gum | 0.04 |
| Carboxyvinyl polymer | 0.3 |
| Compound 1 | 5.0 |
| Perfume | 0.05 |
| Purified water | remainder |
| Total | 100 |

This day essence showed good results in the above-mentioned test.

Example 6

Sun Screen

A sun screen of the present invention was prepared with the following composition according to a conventional manner.

| Components of starting material | Formulation amount (%) |
| --- | --- |
| Ethanol | 10.0 |
| Octyl methoxycinnamate | 7.0 |
| POE•POP modified dimethylpoylsiloxane | 2.0 |
| Fine particle titanium oxide | 5.0 |
| Zinc oxide | 5.0 |
| Methylcyclopolysiloxane | 20.0 |
| Yolk lecithin | 2.0 |
| Compound 1 | 0.01 |
| Perfume | 0.1 |
| Purified water | Reminder |
| Total | 100 |

This sun screen showed good results in the above-mentioned test.

Example 7

Skin Lotion

Skin lotions of the present invention were prepared with the following composition according to a conventional manner.

| Components of starting material | Formulation amount (%) |
| --- | --- |
| Compound 1 | See Table 1 |
| Diisopropylidene-D-sorbitol *1 | See Table 1 |
| Diisopropylidene-xylito l *2 | See Table 1 |
| Glycerin | 5.0 |
| 1,3-Butylene glycol | 5.0 |
| 1,2-Pentane diol | 1.0 |
| Decaglyceryl monolaurate | 0.3 |
| Sucrose monolaurate | 0.3 |
| Carrageenan | 0.1 |
| Citric acid | 0.02 |
| Sodium citrate | 0.08 |
| Perfume | 0.01 |
| Purified water | Reminder |
| Total | 100 |

*1 1,2:5,6-Di-O-isopropylidene-D-glucitol
*2 1,2:4,5-Di-O-isopropylidene-D-xylitol

| | Formulation amount (%) | | | | | |
| --- | --- | --- | --- | --- | --- | --- |
| Component of starting material | Example 7-1 | Example 7-2 | Example 7-3 | Example 7-4 | Example 7-5 | Example 7-6 |
| Compound 1 | — | — | 1.0 | 1.0 | — | 1.0 |
| Diisopropylidene-D-sorbitol | 2.0 | — | 1.0 | — | 1.0 | 0.5 |
| Diisopropylidene-xylitol | — | 2.0 | — | 1.0 | 1.0 | 0.5 |

Each skin lotion showed good results in the above-mentioned test.

Incidentally, in Examples, the perfume with the following perfume formulation was used.

| Perfume Formulation A | |
| --- | --- |
| Component | % by mass |
| Terpineol | 10.00 |
| Terpinyl acetate | 2.00 |
| Cepionate (epimethhyl dihydrojasmonate) | 60.00 |
| Methyl dihydro jasmonate | 250.00 |
| Indol | 0.05 |

-continued

| Perfume Formulation A | |
|---|---|
| Component | % by mass |
| 2-Methyl-3-(3,4-methylene-dioxy-phenyl)-propanal | 3.00 |
| Hydroxy citronellal | 20.00 |
| Hydroxy citronellol | 10.00 |
| p-t-Butyl-α-methylhydro-cinnamic aldehyde | 35.00 |
| 4-(4-Hydroxy-4-methyl-pentyl)-3-cyclohexen-1-carboxyaldehyde | 75.00 |
| 3-Methyl-5-phenylpentanol | 20.00 |
| Phenylethyl alcohol | 10.00 |
| α-Ionone | 10.00 |
| β-Ionone | 20.00 |
| γ-methyl ionone | 10.00 |
| Dihydro-β-ionone | 25.00 |
| Benzyl salicylate | 150.00 |
| cis-3-Hexenyl salicylate | 30.00 |
| Eugenol | 0.80 |
| Cinnamic alcohol | 5.00 |
| Cinnamic aldehyde | 0.50 |
| Guaiol acetate | 1.00 |
| Guaiol | 0.50 |
| Cedrenyl acetate | 5.00 |
| Methyl cedryl ketone | 30.00 |
| 6,7-Dihydro-1,1,2,3,3-pentamethyl-4(5H)-indane | 2.00 |
| Vetiver acetate | 10.00 |
| 3-Methyl-5-(2,3,3-trimethyl-3-cyclopenten-1-yl)-pentan-2-ol | 2.00 |
| 2-Ethyl-4-(2,3,3-trimethyl-3-cyclopenten-1-yl)-2-buten-1-ol | 0.80 |
| Isobornylcyclohexanol | 35.00 |
| Heliotropin | 10.00 |
| Coumarin | 2.00 |
| Vanillin | 2.00 |
| Ethyl vanillin | 0.10 |
| Muscone | 0.50 |
| Ethylene brassylate | 42.00 |
| 4,6,6,7,8,8-Hexamethyl-1,3,4,6,7,8-hexahydrocyclo-pentabenzopyrane | 60.00 |
| Cyclopentadecanolide | 20.00 |
| Ambrettolide | 1.00 |
| γ-Undecalactone | 0.40 |
| γ-Decalactone | 0.10 |
| 4-(4-Hydroxypheny)-2-butanone | 0.50 |
| Musk ketone | 0.10 |
| Skatole | 0.01 |
| cis-Jasmone | 0.05 |
| Phenyl ethyl acetate | 0.10 |
| Civetone | 0.20 |
| γ-Nonalactone | 0.05 |
| α-Santalol | 0.20 |
| β-Santalol | 0.20 |
| Eugenyl acetate | 0.10 |
| α-Hexylcinnamic aldehyde | 20.00 |
| α-Damascone | 0.04 |
| β-Damascone | 0.02 |
| β-Damascenone | 0.01 |
| γ-Damascone | 0.01 |
| Rose absolute | 0.50 |
| Rose oil | 4.50 |
| Sandalwood oil | 2.00 |
| Labdanum absolute | 0.05 |
| Ciste absolute | 0.01 |
| Vetiver oil | 0.50 |
| Guaiac wood oil | 0.10 |
| Total | 1000.00 |

INDUSTRIAL APPLICABILITY

It can be applied to a skin cosmetic, a medical product and a quasi-drug as an external agent, or a bathing agent, etc. As a preparation form thereof, it can be made, for example, a lotion, a milky lotion, a cream, a pack, etc., and it is extremely useful in view of the beauty of the skin.

The invention claimed is:

1. A method for maintaining a skin in a healthy state, comprising applying to the skin a skin cosmetic which comprises a sugar alcohol derivative represented by the following formula (1):

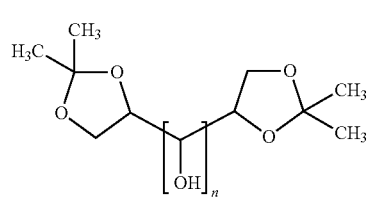

wherein n is 1 to 5.

2. The method according to claim 1, wherein the sugar alcohol derivative is a compound represented by the following formula (2):

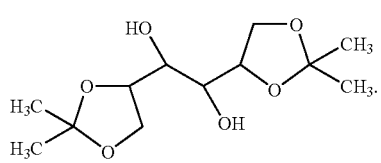

3. The method according to claim 1, wherein the compound represented by the formula (2) is 1,2:5,6-di-O-isopropylidene-D-mannitol.

4. The method according to claim 1, wherein a formulation amount of the sugar alcohol derivative ranges from 0.001 to 10.0% by mass based on the total amount of the skin cosmetic.

5. A method for reducing wrinkles on a skin, comprising applying to the skin an anti-wrinkle agent which comprises a sugar alcohol derivative represented by the following formula (1):

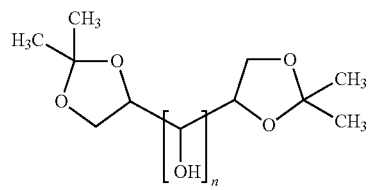

wherein n is 1 to 5.

6. The method according to claim 5, wherein the sugar alcohol derivative is a compound represented by the following formula (2):

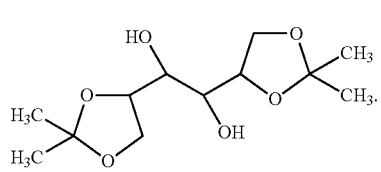

7. The method according to claim 5, wherein the compound represented by the formula (2) is 1,2:5,6-di-O-isopropylidene-D-mannitol.

8. The method according to claim 5, wherein a formulation amount of the sugar alcohol derivative ranges from 0.001 to 10.0% by mass based on the total amount of the anti-wrinkle agent.

9. A skin cosmetic which comprises a sugar alcohol derivative represented by the following formula (1).

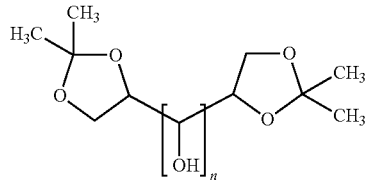

(1)

wherein n is 1 to 5, and a surfactant.

10. The skin cosmetic according to claim 9, wherein the sugar alcohol derivative is a compound represented by the following formula (2):

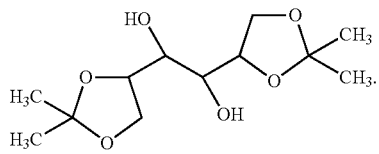

(2)

11. The skin cosmetic according to claim 9, wherein the compound represented by the formula (2) is 1,2:5,6-di-O-isopropylidene-D-mannitol.

12. The skin cosmetic according to claim 9, wherein a formulation amount of the sugar alcohol derivative ranges from 0.001 to 10.0% by mass based on the total amount of the skin cosmetic.

* * * * *